United States Patent [19]

Meyer

[11] 4,183,904

[45] Jan. 15, 1980

[54] RECOVERY OF BORON FROM WASTE STREAMS

[75] Inventor: Oscar A. Meyer, Pensacola, Fla.

[73] Assignee: Monsanto Company, St. Louis, Mo.

[21] Appl. No.: 839,068

[22] Filed: Oct. 3, 1977

[51] Int. Cl.$^2$ ............................................. C01B 35/06
[52] U.S. Cl. ................................. 423/283; 210/71; 260/462 A; 568/821; 568/837
[58] Field of Search ................ 260/586 AB, 462 A; 568/837, 821; 423/283, 278; 210/63 R, 71, 73 R

[56] References Cited

U.S. PATENT DOCUMENTS

| | | | |
|---|---|---|---|
| 3,796,761 | 3/1974 | Marcell et al. | 423/283 |
| 3,946,077 | 3/1976 | Thiel et al. | 568/837 |
| 4,058,565 | 11/1977 | Thiel et al. | 568/837 |

FOREIGN PATENT DOCUMENTS 851568 8/1977 Belgium .

Primary Examiner—Benoît Castel
Attorney, Agent, or Firm—Thomas Y. Awalt, Jr.

[57] ABSTRACT

A method for the recovery of boron compounds from waste streams containing boric acid and combustible organic materials in water by incineration of the combustible organic materials and dehydration of the boric acid to boric oxide. Quenching of the boric oxide, depending upon temperature and water content, yields orthoboric and/or metaboric acids in vapor phase and polyboric acid in liquid phase which is cooled along with the products of the combustion of the organic materials and, in the presence of water, converted to a mixture of boric acids in solid and liquid phase leaving the products of combustion in vapor phase. The mixture of boric acids is then separated from the products of combustion.

7 Claims, 1 Drawing Figure

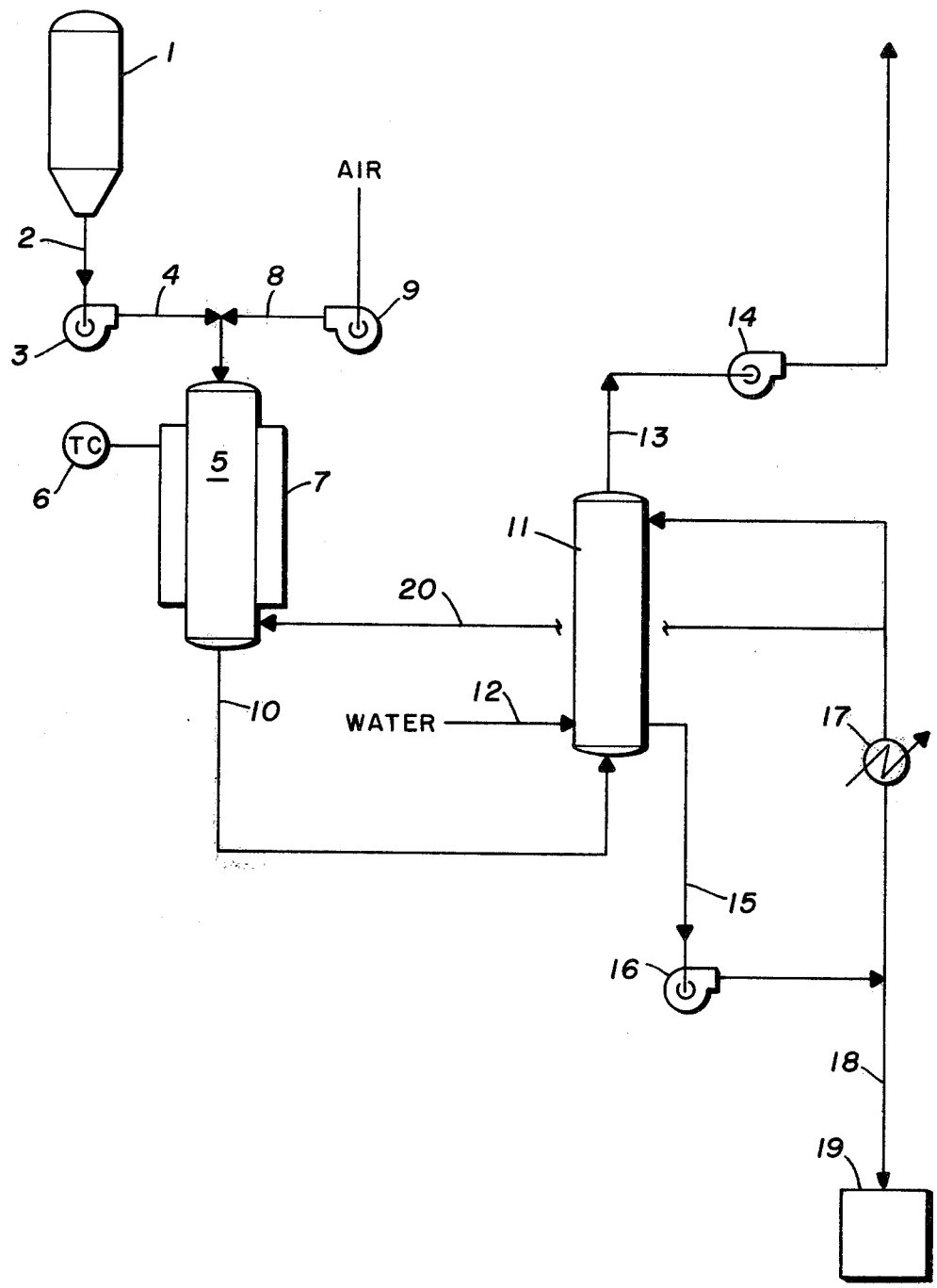

RECOVERY OF BORON FROM WASTE STREAMS

BACKGROUND OF THE INVENTION

1. Field of the Invention

The invention relates generally to a process for recovering boron values from waste streams comprising boric acid and combustible organic materials; and more particularly to a process for the burning of combustible organic materials in the presence of boric acid, thereafter separating and recovering boric acids from the products of combustion.

2. The Prior Art

Incineration and selective recovery of desired elements has long been known as an important part of waste treatment, particularly with respect to sewage. It is well known, for example, that the organic materials in sludges can be disposed of by incineration. Incineration reduces the waste materials to inert ash concomitantly producing gases and vapors, principally carbon dioxide and steam. It is well known that sewage sludges can be calcined under controlled conditions to form calcium oxide solids from the calcium carbonate values. A specific process for recovering calcium values from calcium and phosphate-bearing sludge was patented as U.S. Pat. No. 3,996,133. Such processes involve process means specific to the waste stream element combination or mixture for the recovery of desired materials, which are, for the most part non volatile.

Industrial waste streams containing more volatile compounds such as boric acid are not uncommon. Boric acid and combustible organic materials constitute a substantial portion of the waste stream of a commercial process for the preparation of cyclohexanol and cyclohexanone by boric acid catalyzed oxidation of cyclohexane. The loss of the boric acid is not only wasteful but it is environmentally unacceptable; causing extremely offensive air and surface water pollution. Prior art methods of recovery involve the so-called "wet air oxidation" a liquid phase oxidation process conducted under high pressure and consequently at considerable expense. An efficient atmospheric pressure disposal system with the recovery of boric acid in cyclohexane oxidation waste streams containing boric acid would be a significant advance in the art and is an object of this invention.

SUMMARY OF THE INVENTION

The invention is a method for the recovery of boron compounds from aqueous waste streams having a makeup including boric acid and combustible organic materials by incineration of the combustible organic materials in the presence of the boric acid at about atmospheric pressure to thereby simultaneously burn the combustible organic materials and dehydrate the boric acid to boric oxide; concomitantly hydrating (to equilibrium) the boric oxide to meta and orthoboric acids in vapor phase and polyboric acid in solid or molten liquid phase and cooling the products of combustion and the ortho, meta and polyboric acids in the presence of water thereby to produce boric acids primarily in solid (a small portion in liquid) phase leaving the products of combustion in vapor phase and separating boric acid from the products of combustion.

In the specification, reference will be made to the Drawing in which the Figure is a schematic of an apparatus in which the process of this invention may be accommodated.

DETAILED DESCRIPTION OF THE INVENTION

Any waste stream containing boric acid and combustible organic materials is suitable for the practice of this invention.

A typical waste stream from a boric acid catalyzed cyclohexane oxidation process is characterized as follows:

Density: 1.08 g/cc at 25° C. with a −0.0007 g/cc/°C. temperature coefficient.

Viscosity:
8.6 centistoke at 25° C.
5.3 centistoke at 37° C.
3.6 centistoke at 50° C.
1.8 centistoke at 80° C.

Flash Point: 160° C. in open cup after evaporation of $H_2O$.

Composition:
Boric Acid 5%
Organics 48%
Water 47%

Formula of Organics: $(C_3H_5O)_n$, which is a speculated structure with an average n=5, calculated from organic acidity if monovalent This typical waste stream has already been subjected to one or more boric recovery process steps well known in the art, details of which are not considered essential to the practice of this invention.

By boric acid is meant any one of the many forms of boric acid including orthoboric acid, metaboric acid, polyboric acid, perboric acid, and pyrobroic acid $(H_2B_4O_7)$.

Incineration is accomplished at 600°–1600 ° C., preferably at about 800°–1000° C. After incineration, products of combustion and the boron-containing compounds are cooled to a temperature of about 20°–90° C., preferably 50°–70° C. at which time, in the presence of water, the boric oxide is converted to metaboric and orthoboric acids. The cooling may be a slow cool or a quenching, but quenching is preferred not only because it is faster but because it provides a convenient means of combining the cooling and recovery steps. Quenching with a plurality of fine liquid streams not only cools quickly but provides maximum exposure of the gaseous products of combustion and the molten or solid boron compounds to the quench liquid. Quenching can also be achieved by using the cooled off-gases as the cooling media, accomplishing, in effect, a recycle of the off-gas.

As stated above, the recoverable mixture of boric acids is primarily in solid and/or liquid (molten) phase. The products of combustion, from which the boric acids are to be separated, are, for the most part, in vapor phase. Also present may be residual ash from a less than complete combustion of orgnic materials, unconverted (to boric acid) boric oxides and/or solids present in the waste stream which were part of neither the recoverable mixture of boric acids nor the combustible organic materials. Separation of the vaporous products of combustion from the recoverable mixture of boric acids (without regard for the possible presence of other solids and the possible entrainment of solids in the gases) may be easily accomplished by any convenient means permitting escape of the off-gas. A normally high degree of entrainment of both liquid and solids in the gases will be considerably reduced, however, by employing a gravity settling device or centrifugal separator before relief of the off-gas. Most particles in the off-gas, including the residual ash, boric oxide, boric acids, or foreign solids can be efficiently removed by scrubbing the gases, then settling the solids out of the scrubbing liquid (by gravity or centrifugally). Scrubbing is desirable in order to abate air pollution as well as to increase the efficiency of the recovery process in part, at least, by converting any remaining boric oxides to boric acid. In order to separate the recoverable mixture of boric acids from any such residual ash unconverted boric oxides or foreign matter, it may be desirable to convert to solid phase any materials which may have been dissolved during the scrubbing step in the scrubbing liquid (including undissolved residual ash, boric acids newly converted from the uncoverted boric oxide during scrubbing or foreign matter) thereby to permit recovery of entrained or evaporated (caused by exertion of its vapor pressure) boric acids from the off gas. The residue, including the recoverable mixture of boric acids (with or without the washings of the off-gases), is subjected to conditions fostering dissolution of the solid boric acids so as to permit removal of the undesired ash and any other solids by filtration or centrifugation. The resulting boric acid solution may be returned to the cyclohexane oxidation process or the boric acid recovered in its purest form by concentration, crystallization and separation techniques which are well known to those skilled in the art.

The essential reactions involving boron during the course of incineration, vaporization and recovery are as follows:

During incineration:

$$2H_3BO_3 \longrightarrow B_2O_3 + 3H_2O \quad (1)$$

(orthoboric acid)　　(boric oxide)

During vaporization:

$$B_2O_3 + H_2O \rightarrow 2HBO_2 \text{ (metaboric acid)} \quad (2)$$

and in solid phase:

$$B_2O_3 + XH_2O \rightarrow B_2O_3 \cdot XH_2O \text{ (polyboric acid)} \quad (3)$$

where $X<1.0$

During recovery all species are re-hydrated $$B_2O_3 + 3H_2O \rightarrow 2H_3BO_3 \quad (4)$$

$$\text{and } HBO_2 + H_2O \rightarrow H_3BO_3 \quad (5)$$

$$\text{and } B_2O_3 \cdot XH_2O + (3-X)H_2O \rightarrow 2H_3BO_3 \quad (6)$$

Referring now in detail to the drawing, a waste stream containing boric acid and combustible organic materials is fed from feed vessel 1 via lines 2, pump 3 and line 4 to tubular reactor 5. Tubular reactor 5 passes through tube furnace 7, the temperature of which is controlled by temperature controller 6. Air passes into the system from line 8 employing blower 9 for pressure. From tubular reactor 5, the combustion products and the converted boric compounds pass through line 10 to scrubber 11 to which a cold water supply is fed through line 12. Vapors containing most of the products of combustion pass from scrubber 11 to the atmosphere via line 13 and induced draft fan 14. The liquid emerging from scrubber 11 passes through line 15, moved by recirculating pump 16, and is cooled in heat exchanger 17. A portion of the liquid from the recirculating system is drawn from line 15 through line 18 from the base of tubular reactor 5 for recovered products collecting in vessel 19. Cooled quench solution is also provided in line 20 to keep the bottom of the reactor and line 10 clean of boric compounds and products of combustion. Make-up water is furnished via line 12. Heat exchanger 17, although not essential, is desirable in that it provides for heat recovery of a portion of the high heat of combustion evolved in the process and also serves as temperature control device to prevent pollution of the atmosphere with the volatile boric acid. Heat exchangers may also be placed in line 10 for more effective heat recovery.

In operation, the combustible organic materials are incinerated in tubular reactor 5, and orthoboric acid is converted to boric oxide in equilibrium with the water in the vapor phase from the feed and product of combustion. At the base of tubular reactor 5, water is injected to carry the waste stream through line 10 into scrubber 11. At the base of reactor 5 quench streams of water impinge upon the boric oxide and polyboric acids so as to hydrate to equilibrium the boric oxide and water system. In scrubber 11, the metaboric and polyboric acids are, for the most part, reconverted to orthoboric acid. Gaseous products of combustion are eliminated through line 13.

EXAMPLES

Employing an apparatus substantially as shown in the Drawing (except that reactor 5 was an open vessel), the following examples were run as indicated. Reactor lengths, scrubber type/packing, residence time, air/waste ratio and temperature were varied. The slight variation in feed stock composition resulted from variations in waste stream employed.

TABLE 1

| Example | 1 | 2 | 3 | 4 | 5 | 6 | 7 | 8 |
|---|---|---|---|---|---|---|---|---|
| Reactor: | | | | | | | | |
| Length, inch | 13 | 26 | 26 | 30 | 30 | 30 | 30 | 30 |
| Length, cm | 33 | 66 | 66 | 76 | 76 | 76 | 76 | 76 |
| Diameter, inch | 1.05 | 1.05 | 1.05 | 2.07 | 2.07 | 2.07 | 2.07 | 2.07 |
| Length, cm | 2.67 | → | | 5.26 | → | | | |
| Waste Stream: | | | | | | | | |
| Total, g | 920 | 300 | 3072 | 4049 | 655 | 4715 | 857 | 2913 |
| Rate, g/hr | 613 | 100 | 131 | 225 | 145 | 148 | 122 | 136 |
| % $H_3BO_3$ | 4.02 | 4.54 | 4.54 | 4.54 | 4.54 | 4.54 | 5.45 | 5.45 |
| % TC | 9.84 | 28.1 | 28.1 | 28.1 | 28.1 | 28.1 | 33.0 | 33.0 |
| Air, scf/m cc/min | 0.60 | 0.34 | 0.67 | 0.67 | 0.67 | 0.94 | 0.8 | 0.7 |
| Temperature, °C. | 530 | 875 | 660 | 930 | 920 | 830 | 860 | 900 |
| O/C Atomic Ratio | 3.5 | 4.3 | 6.4 | 3.8 | 5.8 | 8.0 | 7.0 | 5.5 |

TABLE 1-continued

| Example | 1 | 2 | 3 | 4 | 5 | 6 | 7 | 8 |
|---|---|---|---|---|---|---|---|---|
| Air Velocity, ft/sec cm/sec | 4.5 | 3.6 | 5.8 | 1.9 | 1.9 | 2.6 | 2.2 | 2.0 |
| $H_3BO_3$ Recovery, % | 75 | 75 | 69 | 76 | 79 | 70 | 59 | 63 |
| TC Destroyed, % | 80 | 90 | 60 | 52 | 77 | 89 | 98 | 97 |

TC = Total Carbon

In Example 1 the temperature was below that of efficient operation. In Example 2 feed pump problems resulted in less than accurate measurements. In Example 3 the amount of air introduced was considerably higher than in other examples and should be considered excessive.

The examples were conducted with laboratory equipment having a degree of sophistication only necessary to demonstrate the operability of the process. The waste stream was not fully atomized for complete incineration and the reactor was open (and therefore subject to losses at the outset). A closely controlled process will yield the nearly 100% recovery of boric acid which is theoretically obtainable.

I claim:

1. A method for the recovery of boron from waste streams comprising boric acid and combustible organic materials, the method comprising incinerating the combustible organic materials in the presence of boric acid at a temperature of 600°–1600° C. at about atmospheric pressure to thereby simultaneously burn the combustible organic materials to produce products of combustion in vapor phase and dehydrate the boric acid to boric oxide; concomitantly hydrating to equilibrium the boric oxide in the presence of water to metaboric acid in vapor phase and polyboric acid in liquid phase; cooling the products of combustion and the metaboric and polyboric acids in the presence of water to a temperature of 50°–70° C. by quenching the solid and liquid mixture of boric acids with a plurality of fine liquid streams comprising water, whereby, after cooling, the major portion of the boric acid is solidified and hydrated simultaneously, thereby to produce a mixture of boric acids in solid and liquid phase leaving the products of combustion in vapor phase; and thereafter dissolving the solid phase in the water and physically separating the liquid phase from the vapor phase thereby recovering boron in the form of boric acid.

2. The method of claim 1 wherein incineration is accomplished at a temperature of about 800°–1000° C.

3. The method of claim 1 wherein separation and recovery of boric acids from the off gas is assisted by electrostatic precipitation.

4. The method of claim 1 wherein separation of the mixture of boric acids from the off gas is accomplished by decantation or settling.

5. The method of claim 1 wherein separation of the mixture of boric acids from the off gas is accomplished by centrifugal force.

6. The method of claim 1 further including recovering heat from the liquid phase in conjunction with the hydrating step.

7. The method of claim 1 further including recovering heat from off gas in conjunction with the incinerating step.

* * * * *